US008759600B2

(12) United States Patent
Sun et al.

(10) Patent No.: US 8,759,600 B2
(45) Date of Patent: Jun. 24, 2014

(54) REDUCED FLUIDIZATION OF SOLID PARTICLES IN RADIAL FLOW FLUID/SOLID CONTACTING

(75) Inventors: Bing Sun, South Barrington, IL (US); Paul A. Sechrist, South Barrington, IL (US)

(73) Assignee: UOP LLC, Des Plaines, IL (US)

( * ) Notice: Subject to any disclaimer, the term of this patent is extended or adjusted under 35 U.S.C. 154(b) by 444 days.

(21) Appl. No.: 12/824,431

(22) Filed: Jun. 28, 2010

(65) Prior Publication Data

US 2011/0319691 A1    Dec. 29, 2011

(51) Int. Cl.
*C07C 5/333* (2006.01)

(52) U.S. Cl.
USPC ........... 585/659; 585/654; 208/134; 208/146; 208/152; 208/165; 422/218; 422/219; 422/220

(58) Field of Classification Search
USPC .......... 585/654, 659; 208/134, 146, 152, 165; 502/45, 48; 422/218, 219, 220, 232; 34/506
See application file for complete search history.

(56) References Cited

U.S. PATENT DOCUMENTS

| | | | |
|---|---|---|---|
| 2,997,374 A | 8/1961 | Lavender, Jr. et al. | |
| 3,647,680 A | 3/1972 | Greenwood et al. | |
| 3,652,231 A | 3/1972 | Greenwood et al. | |
| 3,692,496 A | 9/1972 | Greenwood et al. | |
| 3,706,536 A * | 12/1972 | Greenwood et al. | 422/634 |
| 3,909,208 A * | 9/1975 | Boret et al. | 422/218 |
| 3,978,150 A * | 8/1976 | McWilliams, Jr. | 585/659 |
| 4,169,879 A * | 10/1979 | Descoins et al. | 422/220 |
| 4,277,444 A | 7/1981 | Van Landeghem | |
| 4,405,562 A | 9/1983 | Zardi et al. | |
| 4,869,808 A * | 9/1989 | Vora et al. | 208/138 |
| 4,959,198 A * | 9/1990 | Koves | 422/220 |
| 5,015,383 A | 5/1991 | Evans et al. | |
| 5,089,115 A | 2/1992 | Koves | |
| 5,130,106 A * | 7/1992 | Koves et al. | 422/216 |
| 5,779,988 A | 7/1998 | Zardi et al. | |
| 6,059,961 A * | 5/2000 | Koves et al. | 208/146 |
| 6,790,415 B2 * | 9/2004 | Petit et al. | 422/619 |
| 7,125,529 B2 | 10/2006 | Ablin | |
| 2002/0131922 A1 | 9/2002 | Sakai | |
| 2006/0171868 A1 | 8/2006 | Filippi et al. | |
| 2007/0060782 A1 | 3/2007 | Ablin | |

(Continued)

FOREIGN PATENT DOCUMENTS

| | | |
|---|---|---|
| EP | 0555777 | 8/1993 |
| EP | 0575315 | 12/1993 |
| EP | 1442786 | 8/2004 |
| EP | 1477220 | 11/2004 |

(Continued)

*Primary Examiner* — Prem C Singh
*Assistant Examiner* — Bradley Etherton
(74) *Attorney, Agent, or Firm* — Mark R Willis (57) ABSTRACT

Apparatuses and methods are disclosed for contacting radially flowing fluids with solid particles (e.g., catalyst) with reduced tendency for fluidization of the particles, and especially a sealing portion of the particles at the top of a particle retention zone disposed between screens at upstream and downstream positions relative to radial fluid flow. Fluidization is reduced or eliminated by offsetting openings of the screens in the axial direction, such that upstream openings in the upstream screen are above highest downstream openings in a downstream stream. The offset in openings imparts a downward flow component to radially flowing fluid, thereby reducing solid particle fluidization without the need to induce a specific pressure drop profile along the entire axial direction of the screens.

17 Claims, 3 Drawing Sheets

(56) References Cited

U.S. PATENT DOCUMENTS

2007/0274880 A1 11/2007 Filippi et al.
2008/0107575 A1 5/2008 Vetter et al.
2009/0154632 A1 6/2009 Naunheimer et al.

FOREIGN PATENT DOCUMENTS

| EP | 1587611 | 10/2005 |
| EP | 1626802 | 2/2006 |
| WO | 2004043586 | 5/2004 |

* cited by examiner

REDUCED FLUIDIZATION OF SOLID PARTICLES IN RADIAL FLOW FLUID/SOLID CONTACTING

FIELD OF THE INVENTION

The present invention relates to processes for horizontal (e.g., radial) flow fluid/solid contacting processes in which fluidization of solid particles (e.g., catalyst) is reduced. Openings in upstream and downstream screens for retaining the solid particulate are offset with respect to their vertical (e.g., axial) positions.

DESCRIPTION OF RELATED ART

A wide variety of industrial applications involve horizontal or radial flow apparatuses for contacting a fluid with a solid particulate. Representative processes include those used in the refining and petrochemical industries for hydrocarbon conversion, adsorption, and exhaust gas treatment. In reacting a hydrocarbon stream in a radial flow reactor, for example, the feed to be converted is normally at least partially vaporized when it is passed into a solid particle catalyst bed to bring about the desired reaction. Over time, the catalyst gradually loses its activity, or becomes spent, due to the formation of coke deposits on the catalyst surface resulting from non-selective reactions and contaminants in the feed.

Moving bed reactor systems have therefore been developed for continuously or semi-continuously (intermittently) withdrawing the spent catalyst from the catalyst retention or contacting zone within the reactor and replacing it with fresh catalyst to maintain a required degree of overall catalyst activity. Typical examples are described in U.S. Pat. No. 3,647,680, U.S. Pat. No. 3,692,496, and U.S. Pat. No. 3,706,536. In addition, U.S. Pat. No. 3,978,150 describes a process in which particles of catalyst for the dehydrogenation of paraffins are moved continuously as a vertical column under gravity flow through one or more reactors having a horizontal flow of reactants. Another hydrocarbon conversion process using a radial flow reactor to contact an at least partially vaporized hydrocarbon reactant stream with a bed of solid catalyst particles is the reforming of naphtha boiling hydrocarbons to produce high octane gasoline. The process typically uses one or more reaction zones with catalyst particles entering the top of a first reactor, moving downwardly as a compact column under gravity flow, and being transported out of the first reactor. In many cases, a second reactor is located either underneath or next to the first reactor, such that catalyst particles move through the second reactor by gravity in the same manner. The catalyst particles may pass through additional reaction zones, normally serially, before being transported to a vessel for regeneration of the catalyst particles by the combustion of coke and other hydrocarbonaceous by-products that have accumulated on the catalyst particle surfaces during reaction.

The reactants in radial flow hydrocarbon conversion processes pass through each reaction zone, containing catalyst, in a substantially horizontal direction in the case of a vertically oriented cylindrical reactor. Often, the catalyst in such a reactor is retained in the annular zone between inner and outer screens in the forms of concentric cylinders. The screens form a flow path for the catalyst particles moving gradually downward via gravity, until they become spent and must be removed for regeneration. The screens also provide a way to distribute gas or liquid feeds to the catalyst bed and collect products at a common effluent or reaction product collection zone. In the case of radial fluid flow toward the center of the reactor, for example, this collection zone may be a central, cylindrical space within the downstream (in this case inner) screen. Regardless of whether the radial fluid flow is toward or away from the center, the passage of vapor is radially through an upstream (outer or inner) screen, the bed of catalyst particles, and through a downstream (inner or outer) screen. Some current state-of-the-art designs for moving catalyst beds, for example, utilize screen made of profile wire (or V-shaped wire) having a triangular cross section to contain the catalyst.

Experience has shown, however, that the top of the bed of the solid particles is susceptible to fluidization by the horizontally moving fluid that passes through the upstream screen, the solid particles, and the downstream screen. This fluidization is a major concern, as it accelerates particle attrition/fines formation and reduces the efficiency of contacting between the phases (e.g., due to bypassing) and therefore the overall process (e.g., hydrocarbon conversion) performance. An excessive production of fines material undesirably increases the overall pressure drop of the fluid/solid contacting process and interferes with the withdrawal of the solid particles in moving bed systems described above. Continued increase of the pressure drop can necessitate suspending the process for maintenance/servicing and the associated, high costs of lost production time.

Current attempts to prevent fluidization at the top of the bed of solid particles have focused on the use of a sealing portion of the particles (e.g., so-called "seal catalyst") in the annular region between the upstream and downstream screens, but above the uppermost or highest openings of these screens. The sealing portion is therefore a top, quiescent section of the annular particle retention zone, positioned above the immediately lower section that is vertically or axially aligned with openings of the screens and therefore subjected to the flow of fluid. In some cases, the use of a sealing portion of the particles may be combined with passing a sealing portion of the fluid (e.g., so-called "seal gas") vertically or axially downward through the particle bed, rather than radially. The flow of the sealing portion of the fluid further reduces the tendency to form localized upward flow currents in the major portion of the fluid flowing generally in the radial direction. A localized upward flow of fluid is normally observed near the upstream screen that is first contacted by the fluid to cause local fluidization of the solid particles at the top of the bed.

The combination of sealing portions of both the solid particles and fluid can provide some benefit in terms of reducing the fluidization problems described above. Nevertheless, by adopting these strategies, the reduction in fluidization is obtained at the expense of greater utilization of both fluid and particulate to provide these additional sealing portions. Moreover, a satisfactory decrease in fluidization of the solid particles is not always realized with conventional methods. A need therefore exists, in the art of radial flow processes for contacting a fluid with a solid particulate, to minimize or eliminate fluidization of the particulate, in addition to the excess volumes or volumetric flows of sealing portions of the solid and fluid.

SUMMARY OF THE INVENTION

The present invention is directed to radial flow processes for contacting fluids with solid particles that effectively control fluidization of the particulate and its adverse consequences as discussed above. More particularly, the invention is associated with the discovery that offsetting the elevations of openings in upstream and downstream screens, used to contain the solid particles, effectively reduces localized upward gas flow near the top of the screens that contributes to fluidization. This offset screen configuration may advantageously be combined with the use of sealing portions of both solid particles and fluid, as discussed above, which further act to hinder undesired fluidization. Therefore, when used according to the present invention, a sealing portion of the solid particles may be a topmost portion above the highest openings of the upstream and downstream screens. In this case, a line segment connecting highest openings of the upstream and downstream screens can define a diagonal base of the sealing portion. A top free surface, which may be curved (e.g., due to the addition of free falling particles from above), or may otherwise be a relatively constant level of solid particles, corresponds to the height of the annular particle retention zone between the screens and above highest openings of both screens. This top free surface can define the top of the sealing portion of solid particles, as well as the top of the entire bed of solid particles. A sealing portion of the fluid may be a portion of the total fluid (e.g., a hydrocarbon feed or oxygen-containing catalyst regenerant) entering a reactor or other type of vessel to contact the solid particles (e.g., a hydrocarbon conversion catalyst), whereby the sealing portion is directed axially downward through the particle retention zone between the screens (e.g., an annular catalyst bed), and is therefore usually directed toward the top of the sealing portion of the particles, as defined above.

The present invention may be advantageously practiced without the need to induce specific pressure drop profiles at various screen elevations, according to conventional teachings for diverting radial fluid flow between the screens in the downward direction. See, for example, U.S. Pat. No. 4,959,198. Therefore, the pressure drop of fluid across one or both of the upstream and downstream screens may be minimized, for example, to a value that is generally less than about 20%, typically less than about 10%, and often less than about 5%, of the pressure drop of radially flowing fluid across the bed of solid particles. According to preferred embodiments, the pressure drop across the upstream screen may be characterized in this manner. In yet other embodiments, the pressure drop of fluid across one or both of the upstream and downstream screens, and preferably the upstream screen, is not graduated as a function of the vertical or axial screen height, or at least not graduated over a major portion of the height.

Accordingly, embodiments of the invention are directed to processes for contacting a solid with a fluid. Representative processes comprise passing at least a portion of the fluid substantially horizontally (e.g., substantially radially) through a bed of solid particles disposed between a vertically oriented upstream screen and a vertically oriented downstream screen. The upstream screen has upstream openings above the highest downstream openings of the downstream screen. Also, the pressure drop of the fluid across each of these screens is as discussed above.

Particular embodiments are directed to processes for radial flow contacting as described above, in which fluid is passed radially radially outward from a central fluid distribution zone, internal to the upstream screen, to a peripheral fluid collection zone external to the downstream screen. While radial outflow is a preferred mode of operation, fluid may also be passed radially inward from a peripheral fluid distribution zone, external to the upstream screen, to a central collection zone, internal to the downstream screen. In either case, the peripheral and central zones within a vertically oriented vessel are annular and cylindrical, respectively.

Other particular embodiments are directed to hydrocarbon conversion processes utilizing radial flow contacting as described above, and representative processes include the catalytic dehydrogenation of paraffinic hydrocarbons (e.g., propane, butane, and/or isobutane) having from 3 to 22 carbon atoms, as well as the catalytic reforming of naphtha petroleum fractions obtained from the fractionation of crude oil.

More specific embodiments of the invention are directed to processes for converting a hydrocarbon feed that is at least partially in the gas phase. The processes comprise passing a major portion of the hydrocarbon feed (e.g., to a central or peripheral fluid distribution zone as described above) substantially radially through solid, hydrocarbon conversion catalyst that is retained in an annular catalyst bed within a vertically oriented vessel. The catalyst is more particularly retained between concentric, cylindrical upstream and downstream screens. The processes further comprise passing a minor, sealing portion of the hydrocarbon feed axially downward from the top of a sealing portion of the catalyst and through the annular catalyst bed. The processes additionally comprise withdrawing a hydrocarbon product (e.g., from a central or peripheral collection zone as described above) that results from contact between the hydrocarbon feed (both the major portion and the sealing portion) and the hydrocarbon conversion catalyst. The processes also optionally comprise adding regenerated hydrocarbon conversion catalyst to the sealing portion of the catalyst and withdrawing spent hydrocarbon conversion catalyst from the bottom of the annular catalyst bed, in order to provide an overall axial, downward flow of the catalyst through the annular catalyst bed or catalyst retention zone. The addition and/or withdrawal of catalyst may be continuous or intermittent. An offset of the openings in the upstream and downstream screens is used, as described above, in order to reduce or eliminate fluidization of the sealing portion of the catalyst. Also, the pressure drop of the hydrocarbon feed across each of the upstream and downstream screens is as described above.

In any of the embodiments described above, the upstream and downstream screens preferably have flow channels formed from one or more elongated particle retention elements (e.g., profile wire).

These and other embodiments and aspects relating to the present invention are apparent from the following Detailed Description.

Figure 1:
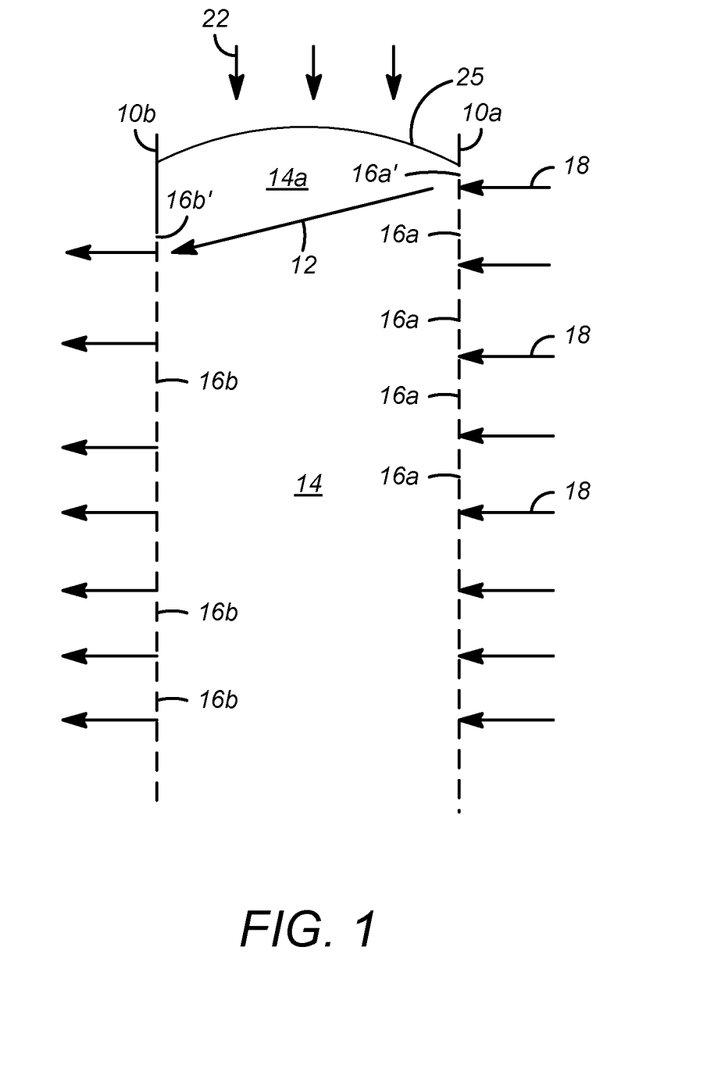
FIG. 1 is a side, cut-out view of representative, vertically oriented upstream and downstream screens that retain solid particles, including a sealing portion above screen openings that are offset.
Figure 2:
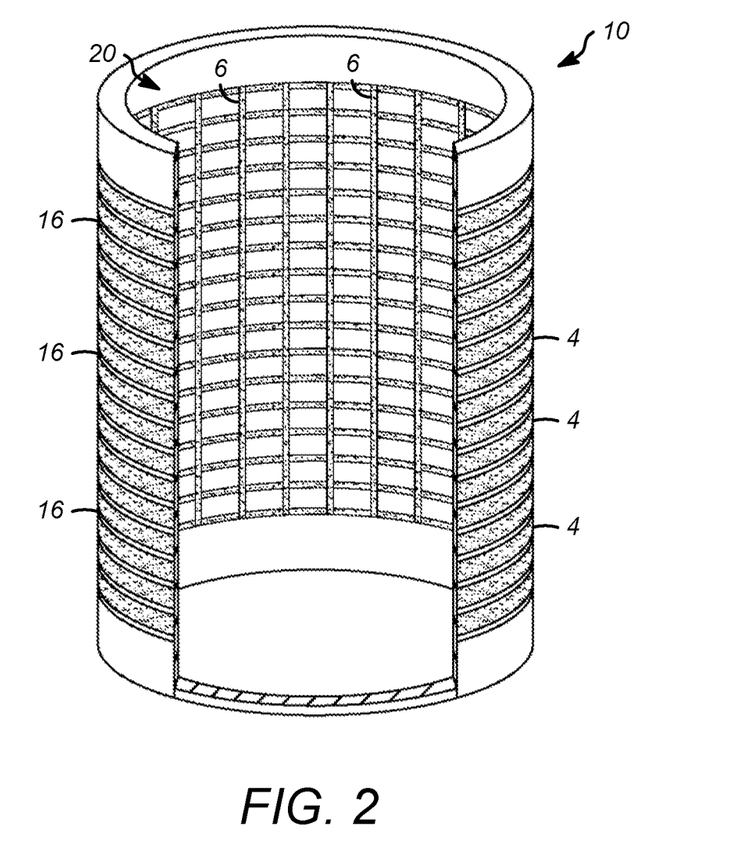
FIG. 2 is a more detailed, front view of a representative, cylindrical profile wire screen, in which flow channels are formed between adjacent, spaced apart profile wires.
Figure 3:
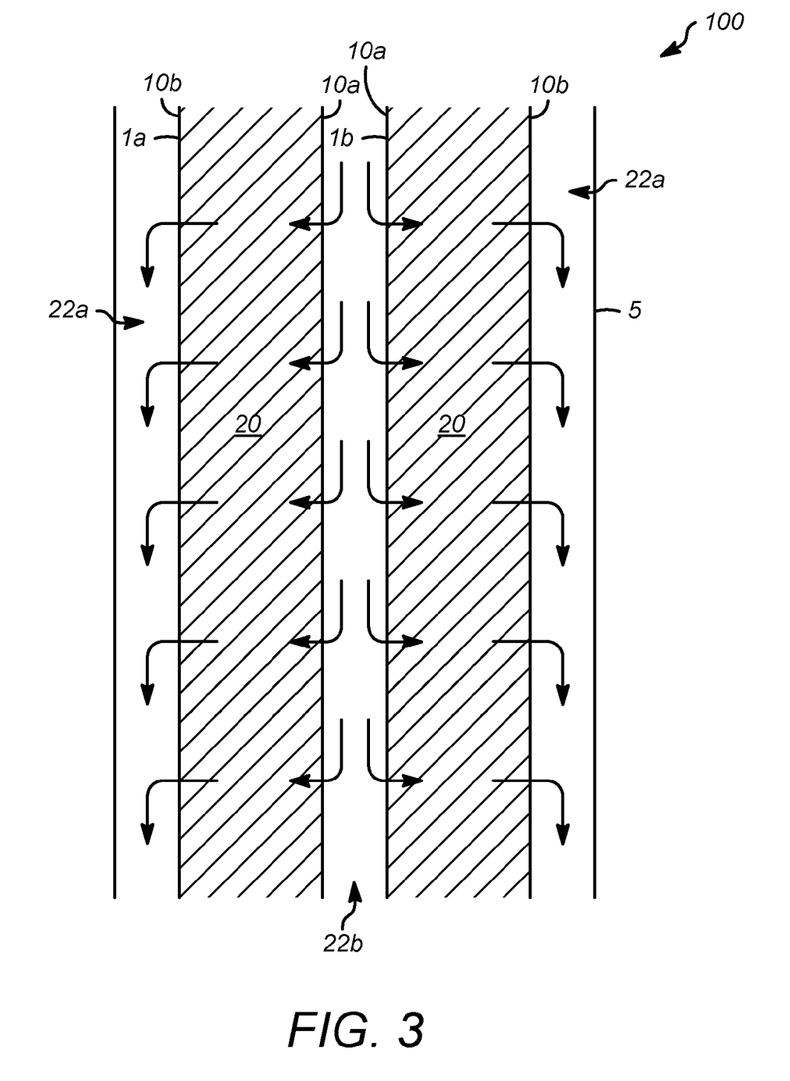
FIG. 3 is a side, cut-out view of a radial flow reactor with inward radial flow and having both upstream and downstream screens disposed therein and an annular catalyst bed retained within the annular space between the concentric, cylindrical screens.

The features referred to in FIGS. 1-3 are not necessarily drawn to scale and should be understood to present an illustration of the invention and/or principles involved. Some features depicted have been enlarged or distorted relative to others, in order to facilitate explanation and understanding. Upstream and downstream screens having highest openings that are offset, as well as radial flow fluid/solid contacting apparatuses and processes utilizing these offset screens, as disclosed herein, will have configurations, components, and operating parameters determined, in part, by the intended application and also the environment in which they are used.

DETAILED DESCRIPTION

Aspects of the invention relate to the configuration of solid particle retention devices, for example screens, for use in apparatuses for the radial flow contacting of fluids (e.g., gases, liquids, or mixed phase fluids containing both gas and liquid fractions) with solids that are typically in particle form (e.g., spheres, pellets, granules, etc.). The maximum dimension (e.g., diameter of a sphere or length of a pellet), for an average solid particle, is typically in the range from about 0.5 mm (0.02 inches) to about 15 mm (0.59 inches), and often from about 1 mm (0.04 inches) to about 10 mm (0.39 inches). An exemplary solid particle is a catalyst used to promote a desired hydrocarbon conversion reaction and normally containing a catalytically active metal or combination of metals dispersed on a solid, microporous carrier.

Catalysts and other solid particles are retained in screens when the smallest widths of the openings (e.g., flow channels), for passage of fluid in the substantially horizontal (e.g., radial) direction, are less than the smallest dimension (e.g., diameter of a sphere or diameter of the base of a pellet), for an average particle. Typical smallest (or minimum) openings (or flow channel widths), for example, formed as gaps between adjacent, spaced apart profile wires or windings of profile wires) are in the range from about 0.3 mm (0.01 inches) to about 5 mm (0.20 inches), and often from about 0.5 mm (0.02 inches) to about 3 mm (0.12 inches). A representative apparatus containing both upstream and downstream screens (e.g., comprising concentric cylinders having an annular catalyst bed or catalyst retention zone between the screens) is therefore a radial flow reactor that may be used in a number of chemical reactions including hydrocarbon conversion reactions such as catalytic dehydrogenation and catalytic reforming.

FIG. 1 illustrates the use of a vertically oriented upstream screen 10a that, in conjunction with vertically oriented downstream screen 10b, retains a bed of solid particles, in a solid particle retention zone 14, between these screens 10a, 10b. As used herein, "retain" or "retention," in describing the condition of the solid particles, refers to its confinement with respect to at least one dimension or direction (e.g., the horizontal dimension or radial direction) and does not preclude its overall movement, for example in the vertical dimension or axial direction. In fact, contemplated applications of the offset screens include their use in radial flow reactors in which the solid particles, often a catalyst used to promote a desired conversion, is in a moving bed that allows the catalyst to be intermittently or continuously withdrawn (e.g., for regeneration by burning accumulated coke) and replaced in order to maintain a desired level of catalytic activity in the reactor. Therefore, the screens may, for example, confine the catalyst in the radial direction (e.g., between an inner radius and an outer radius of an annular retention zone formed by the upstream and downstream screens) but still allow the catalyst to move axially in the downward direction. It is often desired in processes according to the present invention to maintain an axially downward flow of the solid particles, normally from a particle (e.g., fresh or regenerated catalyst) inlet at the top of the particle retention zone to a particle (e.g., spent catalyst) outlet at the bottom of this annular zone. Processes incorporating radial flow, moving bed catalytic reactors are therefore representative of those which may benefit from a reduction in fluidization according to aspects of the invention as described herein. Catalyst addition and withdrawn may be performed continuously or intermittently.

The terms "upstream" and "downstream" refer to the positions of the screens relative to the direction of horizontal (e.g., radial) fluid flow, such that the upstream screen is first contacted with this fluid, followed by the downstream screen. After contacting the upstream screen and before contacting the downstream screen, this horizontally flowing fluid contacts the solid particles disposed between these screens. The terms "axial" and "radial" are used to designate directions with respect to cylindrical vessels, such that, when these vessels are oriented vertically, the "axial" direction is a vertical direction parallel to the axis of the cylinder, whereas the "radial" direction is a horizontal direction along a radius of a circular, horizontal cross section of the cylinder. It is understood that the terms "axial" and "radial" can more broadly refer to vertical and horizontal directions in cases of methods as described herein being performed in vessels and/or with screens having shapes other than cylindrical shapes.

FIG. 1 illustrates an offset between the vertical (e.g., axial) positions of upstream openings 16a of upstream screen 10a and downstream openings 16b of downstream screen 10b. As shown, upstream screen 10a has upstream openings 16a that extend above (e.g., are at a greater axial height relative to) highest downstream openings 16b' of downstream screen 10b. This offset tends to impart a downward flow component to fluid (e.g., a hydrocarbon feed or oxygen-containing catalyst regenerant) after entering the bed of solid particles or solid particle retention zone 14 through upstream screen 10a at upstream openings positioned higher than the highest downstream openings. Therefore, while an upstream flow direction 18 of all, or at least a portion (e.g., greater than about 50%, and often greater than about 90%), of the fluid that contacts solid particle retention zone 14 is substantially horizontal (e.g., substantially radial) prior to entering upstream screen 10a, this fluid exhibits a downwardly biased flow 12, having a downward (e.g., axial) flow component at least in an upper region of the solid particles above highest downstream openings 16b' of downstream screen 10b but below highest upstream openings 16a' of upstream screen 10a. The downward bias in fluid flow hinders fluidization of solid particles near the top of solid particle retention zone 14, thereby mitigating some or all of the drawbacks, as discussed above, that are associated with fluidization in radial flow fluid/solid contacting processes. For example, an effective reduction in fluidization can be achieved when highest upstream openings 16a' are above (i.e., are at an axial height exceeding) highest downstream openings 16b' by a vertical height differential (e.g., an axial distance) generally from about 0.5 times to about 2 times, and typically from about 0.8 times to about 1.8 times, a horizontal spacing distance between the screens, corresponding to the width of the bed of solid particles or solid particle retention zone 14.

Advantageously, reduced fluidization allows for a reduction in the amount of a sealing portion of the solid particles, if used in conjunction with the processes described herein. In the cross-sectional view of the embodiment illustrated in FIG. 1, a base of sealing portion 14a of solid particle retention zone 14 is defined by a line segment connecting highest upstream openings 16a' to highest downstream openings 16b', which base also corresponds to the arrow in FIG. 1 showing downwardly biased flow 12. Sealing portion 14a of solid particles therefore has a diagonal base and extends to the top of both upstream and downstream screens 10a, 10b and consequently to the top of solid particle retention zone 14. Sealing portion 14a also has a top free surface 25, all or a portion of which is generally above highest upstream openings 16a' of upstream screen 10a. By offsetting upstream and downstream screens 10a, 10b as described herein, a minimum depth of sealing portion 14a, i.e., the vertical, for example axial, distance from highest upstream openings 16a' of upstream screen 10a to the top of solid particle retention zone 14, is generally less than the horizontal spacing distance between the screens, or width of the solid particle retention zone 14. Typically, this minimum depth of sealing catalyst is less than about 0.8 times, and often less than about 0.5 times, this width.

Offsetting of the screens alleviates the problem, as discussed above, of upward fluid flow near the top of solid particle retention zone 14, and/or in sealing portion 14a of this zone, which would otherwise render the solid particles susceptible to fluidization. It has been determined that, according to particular embodiments of the invention, none of the solid particles become fluidized if at least some, as particles defining top free surface 25, reside above highest upstream openings 16a' of upstream screen 10a. Preferably all of top free surface 25 resides above highest upstream openings 16a', as shown in FIG. 1. These findings, associated with offsetting the upstream and downstream screens, are exploited in processes of the present invention, not only in terms of easing concerns related fluidization, but also of allowing a reduction in depth of the sealing portion 14a of the solid particles. A reduction in bed depth can translate to an increase in unit capacity in the case of a revamp of an existing radial flow process, or otherwise a reduction in overall elevation of the solid particle retention zone 14 and associated equipment (e.g., a vessel and screens).

Alone or in combination with sealing portion 14a of the solid particles, a sealing portion of the fluid (e.g., a hydrocarbon feed or an oxygen-containing catalyst regenerant) may be introduced from directly above the solid particle retention zone 14 and passed through the zone, often having an annular configuration, with a substantially axially downward flow 22. Unlike the sealing portion of the fluid, therefore, the major portion of the fluid has a substantially horizontal (e.g., radial) upstream flow direction 18. The flow of the sealing portion relative to the flow of total fluid introduced into the bed of solid particles (in any flow direction) (e.g., the flow of the sealing portion relative to the combined flow of the sealing portion and the major portion flowing substantially horizontally) is generally less than about 10%, typically less than about 5%, and often less than about 2% of this total or combined flow. The sealing portion of the fluid generally hinders fluidization by exerting a downward force on particles at or near the top of the particle retention zone 14. In some cases, however, fluidization may be adequately controlled even without the use of a sealing portion.

As noted above, a significant consideration is the ability to impart a downward flow component in fluid flowing through the bed of solid particles at or near axial elevations corresponding to highest upstream and downstream openings 16a', 16b' of upstream and downstream screens 10a, 10b. Importantly, the advantages in terms of reduced fluidization can be realized without the need to induce a specific pressure drop profile (e.g., a graduated pressure drop as a function of axial length) over the entire, or even a significant, vertical height of upstream and/or downstream screens 10a, 10b. Therefore, the pressure drop across at least one of the upstream and downstream screens is minimized, and in preferred embodiments is less than about 10% (e.g., in the range from about 0.01% to about 10%) of the pressure drop across the bed of solid particles. Typically, this pressure drop is less than about 5%, and often less than about 3%, of the pressure drop across the bed of solid particles. Otherwise the pressure drop from (i) the point that the major portion of fluid, flowing substantially horizontally, first impacts any part connected to the upstream and/or downstream screen (e.g., to induce a pressure drop) or other type of particle retention element to (ii) the point that this major portion of fluid first enters the solid particle retention zone 14, or first contacts the solid particles may also be within these percentage ranges, relative to the pressure drop across the bed of solid particles.

Preferred radial flow processes according to the present invention involve the use of cylindrical, vertically oriented vessels that contain the upstream and downstream screens that are also cylindrical and disposed concentrically. In such embodiments, solid particles are retained between the screens in an annular particle retention zone. The upstream and downstream screens have the ability to not only retain solid particles such as catalysts but also effectively distribute radially or horizontally flowing fluids to these particles. Although the screens are described herein primarily with respect to their exemplary use in radial flow reactors, it is understood that the advantages of offsetting the screens is broadly applicable to a wide variety of apparatuses and methods for fluid/solid contacting. Illustrative examples include filtration, selective gas or liquid adsorption (e.g., pressure swing adsorption or the adsorptive separation of liquids), reactive distillation, and others.

A representative screen, which may be used as an upstream screen or a downstream screen, is depicted in FIG. 2. Screen 10 has a cylindrical shape that may be positioned, for example concentrically, within a radial flow reactor having an outer, cylindrical vessel (not shown). A plurality of openings 16 in this embodiment are flow channels formed on an outer surface as gaps between a plurality of elongated particle retention elements 4. Retention elements 4 are spaced apart along the axial length of the cylindrical screen, which may correspond to the axial length of the vessel in which the screen 10 is disposed. As shown in FIG. 2, openings 16 in the form of flow channels may have constant widths at the outer surface of the screen and be spaced apart at constant intervals. Both the elongated particle retention elements 4 and flow channels 2 formed between them extend circumferentially in circular shapes at constant axial positions and spaced apart in the axial direction, with these shapes corresponding to the circular cross section of the cylinder. It is possible for the circumferentially elongated particle retention elements 4 to extend about the perimeter, or at least part of the perimeter, of other shapes, for example ovals or polygons, defining a radial boundary of an adjacent particle retention zone 20. Fluid from the interior or exterior of screen 10 is therefore directed in a radial or horizontal flow direction through openings 16 in the form of flow channels, passing from the outer surface to an inner surface. According to further embodiments, the elongated particle retention elements and flow channels formed between them may extend axially rather than circumferentially.

A representative type of circumferentially elongated particle retention element 4 used for upstream and/or downstream screen 10 is profile wire. Profile wire screen is often fabricated with the wires surrounding, and welded to, a cage of longitudinal support rods 6. The profile wire, as a type of circumferentially extending particle retention element 4, extends about the perimeter (circumference) of a circle defining an inner or outer radial boundary of annular particle retention zone 20 disposed between screen 10 and another upstream or downstream screen (not shown). Typically, the profile wire has a triangular cross section, with triangular bases forming a smooth surface on one side of the profile wire screen, which is normally the side adjacent to the solid particles, and triangular vertices forming an edged surface on the opposite side of the screen, which is normally the side adjacent an open space such as an annular or central fluid distribution zone or fluid collection zone, as described below with respect to hydrocarbon conversion processes.

In an alternative embodiment, a single elongated particle retention element 4 such as profile wire is wound in a spiral shape, and openings 16, namely flow channels, are formed between adjacent, spaced apart windings. In this embodiment, flow channels are effectively formed between each complete turn of the windings to provide the equivalent of multiple flow channels, although actually only a single flow channel extends in the spiral shape. While the flow channels formed in this embodiment extend circumferentially, they are not horizontal as in the embodiment of FIG. 2, but are instead somewhat pitched in the axial direction. The axial pitch may deviate from a constant axial position (e.g., constant horizontal height or plane), for example by less than about 25°, and often less than about 10°.

Still further embodiments of the invention are directed to hydrocarbon conversion processes utilizing radial flow reactors that contain the upstream and downstream screens having an offset configuration and the pressure drop characteristics as discussed above. In exemplary processes, a major portion of a hydrocarbon feed stream, at least partially in the gas phase, is passed, either substantially radially inward or substantially radially outward, through an annular bed of solid catalyst particles disposed between the screens. Outflow operation is preferred. A minor sealing portion of the hydrocarbon feed may be passed axially downward from the top of a sealing portion of the catalyst (i.e., the "seal catalyst") through the annular catalyst bed. The processes further comprise withdrawing a hydrocarbon product resulting from the contact between both the major portion and seal portion of the hydrocarbon feed with the hydrocarbon conversion catalyst. Exemplary processes also comprise adding regenerated hydrocarbon conversion catalyst to the sealing portion of the catalyst and withdrawing spent hydrocarbon conversion catalyst from the bottom of the annular catalyst bed. The adding and withdrawing of the catalyst may be performed, for example, either continuously or intermittently.

The hydrocarbon product stream may be withdrawn, for example, from the catalyst bed through a cylindrical fluid collection zone at the center of the reactor (e.g., internal to downstream screen, in the case of an inwardly flowing hydrocarbon feed stream, or otherwise through an annular fluid collection zone at an inner periphery of the reactor (e.g., external to the downstream screen), in the case of an outwardly flowing hydrocarbon feed stream. A representative radial flow process is used to dehydrogenate paraffinic hydrocarbon streams containing a saturated hydrocarbon, or a combination of saturated hydrocarbons, in the $C_3$ to $C_{22}$ carbon number range, to provide a corresponding mono-olefin or combination of mono-olefins. Another representative process is a catalytic reforming process used to increase the octane number of a naphtha petroleum fraction, or a hydrocarbon feed stream comprising hydrocarbons boiling in the range from about 80° C. (180° F.) to about 205° C. (400° F.).

Further representative embodiments of the invention are directed to radial flow reactors, including moving bed reactors, comprising a vessel and screens having a offset configuration, as described herein. The screens are disposed in the vessel to promote the desired fluid/solid particle contacting. In many cases, the vessel and screens will be cylindrical, with the vessel and screens being positioned concentrically, and often with their common axes extending vertically. Other geometries for the vessel and/or screens, for example, conical, or cylindrical with one or more conical ends, are possible.

The screens may also be used in reactors having cross-sectional shapes that are not circular, for example oval or polygonal. Normally, the cross-sectional shapes of the vessel and screens will be the same (although smaller in size in the case of the particle retention device) at any common axial position within the vessel, in order to promote radial flow uniformity.

As discussed above, however, the use of both outer and inner screens can be advantageous for not only distributing the inlet fluid such as a hydrocarbon-containing feed to, but also for collecting the outlet fluid such as a hydrocarbon-containing product from, the particle retention zone 20. FIG. 3 illustrates the use of both upstream screen and downstream screen 10a, 10b, both disposed in a radial flow reactor 100 and having an offset configuration with respect to their openings, as shown in FIG. 1. Cylindrical vessel 5 and screens 10a, 10b are all oriented vertically as shown and disposed concentrically with respect to each other. Particle retention zone 20 in this case is an annular zone between upstream and downstream screens 10a, 10b. The annular space external to downstream screen 10b and within cylindrical vessel 5 may, as discussed above, be a fluid collection zone 22a for recovering fluid exiting the particle retention zone 20 through downstream screen 10b in the case of fluid flowing outwardly as shown by arrows in FIG. 3, or, alternatively, may be a fluid distribution zone in the case of fluid flowing radially in the opposite direction (i.e., inwardly). Conversely, the central space, in the fluid flow configuration shown in FIG. 3 may be a central fluid distribution zone 22b for distributing fluid axially to upstream screen 10a or may be a central fluid collection zone in the case of radial fluid flow in the opposite direction. Flow arrows in FIG. 3 illustrate radial fluid flow through upstream and downstream screens 10a, 10b and also through annular particle retention zone 20, but an overall downward flow of feed distributed to, and product collected from, the particle retention zone 20.

Overall, aspects of the invention are associated with offset screens such as profile wire screens, in which an upstream screen has openings above (i.e., at a greater axial height relative to) highest downstream openings in a downstream screen for use in radial flow reactors. Representative profile wire screens have a smooth first surface defined by triangular bases and an opposing second surface defined by triangular vertices extending radially and spaced apart axially. Those having skill in the art, with the knowledge gained from the present disclosure, will recognize that various changes could be made in the above screens, as well as radial flow fluid/solid particle contacting apparatuses and processes utilizing these screens, without departing from the scope of the present disclosure.

The following example is set forth as representative of the present invention. This example is not to be construed as limiting the scope of the invention as other equivalent embodiments will be apparent in view of the present disclosure and appended claims.

EXAMPLE 1

Fluidization of solid particles was studied in radial flow fluid/solid contacting. A vertically oriented cylindrical vessel containing vertically oriented, cylindrical upstream and downstream screens and solid particles retained in an annular space between the screens was used in the study. Radially flowing fluid was passed through the upstream screen, particle bed, and downstream screen in experiments in which the screens (i) had an offset configuration, with openings in the upstream screen being above the openings in the downstream screen and (ii) did not have this configuration, with highest openings in both screens being at approximately the same axial height.

The results showed that, using the offset screen configuration, the average depth of a sealing portion of the catalyst could be reduced relative to the alternative of using the non-offset or conventional configuration. In fact, using the offset screen configuration, even a nominal amount of solid particles above the highest upstream openings the upstream screen was sufficient to prevent particle fluidization.

The invention claimed is:

1. A process for converting a fluid hydrocarbon feed at least partially in the gas phase, the process comprising:
   (a) passing a major portion of the hydrocarbon feed substantially radially through solid particles of hydrocarbon conversion catalyst retained in an annular catalyst bed between concentric, cylindrical upstream and downstream screens;
   (b) passing a minor sealing portion of the hydrocarbon feed axially downward from the top of a sealing portion of the catalyst and through the annular catalyst bed;
   (c) withdrawing a hydrocarbon product resulting from contact between the major portion and sealing portion of the hydrocarbon feed with the hydrocarbon conversion catalyst;
   (d) adding regenerated hydrocarbon conversion catalyst to the sealing portion of the catalyst; and
   (e) withdrawing spent hydrocarbon conversion catalyst from the bottom of the annular catalyst bed;
   wherein the upstream screen has openings above highest downstream openings of the downstream screen, wherein a base of a sealing portion of the solid particles is defined by a downwardly sloping line segment from highest upstream openings to the highest downstream openings,
   wherein a ratio of a) a vertical distance from highest upstream screen openings to a top of the sealing portion to b) a horizontal spacing distance between the upstream screen and the downstream screen is less than about 0.8, and
   wherein a pressure drop of the fluid across each of the upstream and downstream screens is less than about 10% of a pressure drop across the bed of the solid particles.

2. The process of claim 1, wherein the pressure drop of the fluid across the upstream screen is less than about 5% of the pressure drop across the bed of the solid particles.

3. The process of claim 1, wherein highest upstream openings are above the highest downstream openings by a vertical height differential from about 0.5 to about 2 times the horizontal spacing distance between the screens that defines a depth of the bed of the solid particles.

4. The process of claim 3, wherein the vertical height differential is from about 0.8 to about 1.8 times the horizontal spacing distance between the screens.

5. The process of claim 1, comprising passing the fluid radially within, and with respect to, a vertically oriented vessel containing the upstream and downstream screens.

6. The process of claim 5, comprising passing the fluid radially inward from a peripheral fluid distribution zone, external to the upstream screen, and to a central collection zone, internal to the downstream screen.

7. The process of claim 5, comprising passing the fluid radially outward from a central fluid distribution zone, internal to the upstream screen, to a peripheral fluid collection zone, external to the downstream screen.

8. The process of claim 5, wherein the vertically oriented vessel and the upstream and downstream screens are cylindrical.

9. The process of claim 8, wherein the upstream and downstream screens have flow channels formed from one or more elongated particle retention elements.

10. The process of claim 9, wherein the elongated particle retention elements extend circumferentially about the axes of the cylindrical upstream and downstream screens.

11. The process of claim 10, wherein the elongated particle retention elements comprise profile wires having a triangular cross section, and wherein the flow channels are formed between adjacent wires.

12. The process of claim 8, wherein the solid particles are retained in an annular particle retention zone between the upstream and downstream screens, the process further comprising flowing the solid particles axially.

13. The process of claim 12, the process further comprising passing a sealing portion of the fluid axially downward through the annular particle retention zone.

14. The process of claim 1, wherein the hydrocarbon-containing feed comprises a paraffinic hydrocarbon having from 3 to 22 carbon atoms, and wherein the process is a catalytic dehydrogenation process.

15. The process of claim 1, wherein the hydrocarbon-containing feed comprises a naphtha petroleum fraction and wherein the process is a catalytic reforming process.

16. The process of claim 1, wherein the major portion of the hydrocarbon feed is passed substantially radially outward.

17. The process of claim 1, wherein the ratio a) to b) is less than about 0.5.

* * * * *